United States Patent [19]

Battiste

[11] 4,183,879
[45] Jan. 15, 1980

[54] DIPHOSPHONIC ACIDS AND ESTERS OF PARA-MENTHANE

[75] Inventor: David R. Battiste, Bartlesville, Okla.

[73] Assignee: SCM Corporation, New York, N.Y.

[21] Appl. No.: 924,165

[22] Filed: Jul. 13, 1978

[51] Int. Cl.$^2$ .............................. C07F 9/38; C07F 9/40
[52] U.S. Cl. ...................................... 260/932; 106/300
[58] Field of Search .......................................... 260/932

[56] References Cited

U.S. PATENT DOCUMENTS

| | | | |
|---|---|---|---|
| 2,642,461 | 6/1953 | Morris et al. | 260/932 |
| 3,141,788 | 7/1964 | Whately | 106/300 |
| 3,343,974 | 9/1967 | Faulkner et al. | 106/300 |
| 3,556,828 | 1/1971 | Durrant et al. | 106/300 |

OTHER PUBLICATIONS

Francois et al.; C. P. Acad. Sc., Paris, Serie C, 117–119 (7/15/74).
Trecker et al.; JACS, vol. 85, pp. 3204–3212 (1963).
Collot et al.; Can. J. Chem., vol. 49, pp. 500–504 (1971).
Stiles et al.; J.A.C.S., vol. 80; pp. 714–716 (1951).
Pudovik et al.; Zhur. Obshchei Khim., vol. 29, pp. 3338–3342 (1959).
Kenney et al.; J. Org. Chem., vol. 39, pp. 682–686 (1974).
Quesnel et al.; Compt. Rend., vol. 251, pp. 1074–1076 (1960).
Kenney et al.; J. Org. Chem., vol. 39, No. 5, pp. 682–686 (1974).
Francois et al.; C. R. Acad. Sci., Ser. C, vol. 279, No. 3, pp. 117–119 (1974).

*Primary Examiner*—Mary C. Lee
*Attorney, Agent, or Firm*—Merton H. Douthitt

[57] ABSTRACT

Disclosed are novel diphosphonic acids and diphosphonic acid esters of para-menthane which may be prepared by reacting α-pinene or β-pinene with a dialkyl hydrogen phosphite under effective free-radical conditions.

These products are potentially useful as flame retardants and are useful as treating agents for improving the pigmentary properties of pigmentary titanium dioxide in thermoplastic formulations.

7 Claims, No Drawings

DIPHOSPHONIC ACIDS AND ESTERS OF PARA-MENTHANE

BACKGROUND OF THE INVENTION

The present invention relates to novel diphosphonic acids and diphosphonic acid esters of para-menthane and to their production.

Kenney and Fisher report in *J. Org. Chem.*, Vol. 39, No. 5, pages 682–686 (1974) that the reaction of β-pinene with diethyl hydrogen phosphite in the presence of di-tertiary-butyl peroxide yields a monophosphonate (diethyl-para-menth-1-en-7-ylphosphonate). Under the same reaction conditions using α-pinene, a monophosphonate also was formed (diethyl-para-menth-1-en-6-ylphosphonate). Similarly, Francois and Lalande report in *C. R. Acad. Sci., Ser. C.*, Vol. 279, No. 3, pages 117–119 (1974), that these same monophosphonate products can be made using benzoyl peroxide and di-tertiary-butyl peroxide to catalyze the reaction.

The present invention discloses the novel diphosphonic acids and diphosphonic acid esters of para-menthane. These products are potentially useful as flame retardants and are useful as treating agents for improving the pigmentary properties of pigmentary titanium dioxide in thermoplastic formulations.

BROAD STATEMENT OF THE INVENTION

The instant compounds are diphosphonates and diphosphonic acids of para-menthane and can be represented conventionally by the following structures:

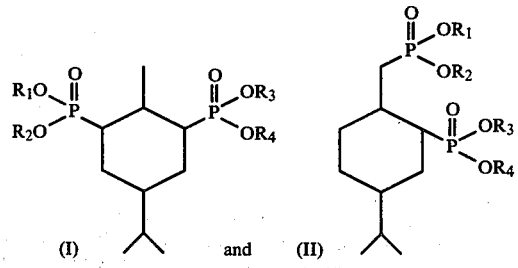

where $R_1$, $R_2$, $R_3$, and $R_4$, independently are hydrogen or a $C_1$-$C_{10}$ alkyl group. For convenience in this application, nomenclature will be based upon the para-menthane skeleton or carbon-nucleus according to the following

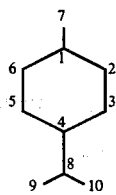

Thus, the instant compounds are 2,6-, and 2,7-diphosphonates or diphosphonic acids of para-menthane.

DETAILED DESCRIPTION OF THE INVENTION

The novel compounds of the present invention can be conveniently prepared by adding a dialkyl hydrogen phosphite to a para-menthene monophosphonate, i.e. a dialkyl para-menth-1-en-6-ylphosphonate or a dialkyl para-menth-1-en-7-ylphosphonate. Such reaction is conducted under free radical conditions at temperatures of about 50° to 200° C. for about 0.1 to 10.0 hours until the desired diphosphonate product is formed. The monophosphonate adducts can be prepared according to the procedures reported by Kenny et al and Francois et al, cited above and incorporated herein.

Alternatively, the diphosphonates or diphosphonic acid esters can be directly prepared by reacting α-pinene or β-pinene with dialkyl hydrogen phosphite under effective free radical conditions for formation of the desired products. Reaction conditions for this procedure include temperatures of 50° to 200° C. and reaction times of 0.1 to 10.0 hours. Free radical conditions in the reaction mixture are established by the addition of a free radical initiator to the reaction mixture. The free radical initiator may be gaseous oxygen typically at a partial pressure ranging from as low as about 1 psig up to as high as about 400 psig, though a wide variety of conventional free radical initiators preferably are used in the present process. Typical of these free radical initiators include various peroxides such as di-tertiary-butyl peroxide, hydrogen peroxide, benzoyl peroxide, and the like. Other well-known free radical initiators will be readily apparent to those skilled in the art. Generally, from about 0.1 to about 10 mole-% (basis α- or β-pinene) of the free radical initiator is used in the reaction mixture. Additionally, ultraviolet radiation may serve to establish the free radical condition, including when a UV photoinitiator is added to the reaction mixture.

While the foregoing reaction appears to parallel the procedures reported by Kenney et al and Francois et al, applicant theorizes that the ability to make the diphosphonate products may at least in part depend upon use of an active initiator in the process. Thus, it is conceivable, though unproven experimentally, that use of an under-strength or stale initiator may permit production of only a monophosphonate product. Also, reaction temperature and particular initiator used may play an important role in synthesizing the diphosphonate products of this invention. Regardless of the theoretical explanation, the instant diphosphonate products can be synthesized by the procedure outlined above as the Examples will demonstrate.

In such disphosphonate production, atmospheric pressure is preferred, though sub-atmospheric and super-atmospheric pressure may be useful as is necessary, desirable, or convenient. Also, non-participating or non-interfering solvents may be used, especially those solvents in which the α-pinene and β-pinene reactants are soluble, but their presence is unnecessary in the process.

The instant diphosphonic acid esters can be converted into their corresponding diphosphonic acids by the addition of a protic acid, acid ion exchange chromotography, or the like. Suitable protic acids include HCl, $HNO_3$, $H_2SO_4$, and the like. Of course, only a partial hydrolysis of the diphosphonates leads to a variety of partial esters of the diphosphonic acids as will be appreciated by those skilled in the art.

The following examples show in detail how the present invention can be practiced but should not be construed as limiting. In this application the metric system of units will apply unless otherwise expressly noted.

EXAMPLE 1

Preparation of tetraethyl-para-menthane-2,6-diyldiphosphonate

To a 5-liter vessel equipped with a mechanical stirrer was added 863 ml (6.7 mol) of diethyl hydrogen phosphite (DEHP). The stirred DEHP was heated to 140° and then 12.3 ml (0.067 mol) of di-tertiary-butyl peroxide was added. Finally, α-pinene, 211 ml (1.3 mol), was added dropwise over a period of 10–30 minutes while the reaction temperture was maintained at 140°–150°. This mixture was heated for 5 hours at 140°, cooled at room temperature, and then distilled in vacuo to yield 54.2 g (0.2 mol; 15.4%) of diethyl para-menth-6-en-2-ylphosphonate, bp = 180°–185° (1.2 mm), and 376.5 g (0.91 mol, 70.0%) of tetraethyl-para-menthane-2,6-diyl-diphosphonate), bp = 198° (0.4 mm). The NMR spectrum showed an $A_2B_3$ pattern corresponding to the ethyl groups at $4.12\delta$ and $1.35\delta$ along with the remainder of the proton signals between $2.5\delta$ and $0.8\delta$.

EXAMPLE 2

Preparation of para-Menthane-2,6-diphosphonic Acid

To a 2-liter distillation flask equipped with a stirrer was added 221 g (0.54 mol) of tetraethyl-para-menthane-2,6-diyldiphosphonate and 442 ml (5.4 mol) of concentrated hydrochloric acid. The reaction mixture was heated at reflux for 15 hours. The solid that precipitated upon cooling of the reaction mixture was filtered and dried in vacuo over phosphoric anhydride. To the remaining solution was added 500 ml toluene and the water removed by azeotropic distillation. Then the toluene was removed by distillation and the crystals obtained dried in vacuo over phosphoric anhydride. The total yield of crystals and precipitated solid was 0.54 mols (100% yield) of the desired diphosphonic acid. The product may be recrystallized from tertiary-butyl alcohol: mp 185°; NMR: (DMSO)$\delta 8.25$ (4bs, 4H,

exchangeable with $D_2O$), 3.6–0.6 (envelope, 18H).

EXAMPLE 3

Preparation of Tertaethyl-para-menthane-2,7-diyldiphosphonate

To a 1-liter reaction flask equipped with a stirrer and nitrogen inlet was added 349 g of diethyl hydrogen phosphite. This material was heated to 140° and 4.6 ml of di-tertiary-butyl peroxide was added. Under stirring, 69.3 g of β-pinene was added dropwise over a period of 35 minutes. The reaction mixture then was maintained at 140° for 3½ hours. During the addition of β-pinene, the reaction was exothermic, sustaining itself at a temperature of 140°–145° for the first 20 minutes of addition. Upon completion of the heating period, the mixture, which consisted of 38.4% unreacted diethyl hydrogen phosphite and 54.9% product, was subjected to distillation providing the pure di-adduct in 89% isolated yield, b.p. = 180° (0.25 mm). The NMR spectrum showed the ethyl groups at $4.02\delta$ and $1.28\delta$ and the remaining protons between $2.6\delta$ and $0.7\delta$.

EXAMPLE 4

Preparation of Tetrabutyl para-menthane-2,6-diyldiphosponate

Dibutyl hydrogen phosphite and α-pinene were reacted in substantially the same manner as reported in Example 3 to make the titled compound (69% theory yield). The NMR spectrum was in agreement with the expected structure.

EXAMPLE 5

Preparation of Tetramethyl para-menthane-2,6-diyldiphosphonate

In a manner similar to the previous examples, 233 ml of dimethyl hydrogen phosphite was stirred with 4.6 ml of di-tertiary-butyl peroxide at 140°–150° while α-pinene (81 ml) was added over a period of 15 minutes. After maintaining the reaction mixture at 140° for 18 hours, an additional 4.6 ml of di-tertiary-butyl peroxide was added. After heating an additional 30 minutes, the reaction mixture was subjected to distillation which provided the di-adduct. The NMR spectrum showed the methyl ester groups as a multiplet consisting mainly of 2 spikes at $3.70\delta$ and $3.88\delta$ along with the remainder of the protons between $0.7\delta$ and $3.5\delta$.

EXAMPLE 6

Preparation of 2-diethoxyphosphinyl-6-dimethoxyphosphinyl para-menthane

In order to form the mixed di-ester, 152 ml of dimethyl hydrogen phosphite was heated to 140°–145° in a 500 ml reaction vessel equipped with a stirrer. Di-tertiary-butyl peroxide (3 ml) was added to the vessel, followed by the addition of 90 g of diethyl para-menth-1-en-6-ylphosphonate. After stirring at this reaction temperature for 9 hours, distillation provided 2.2 g of unreacted mono-ester and 79.4 g of the desired mixed di-ester, b.p. = 236–241 (10 mm). The NMR spectrum was consistent with the expected structure.

I claim
1. A compound selected from

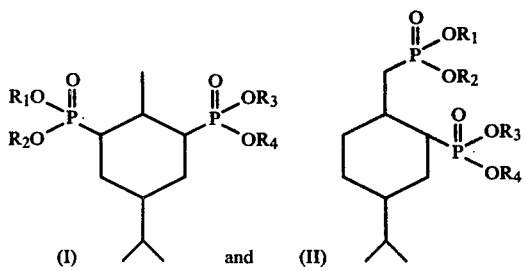

where $R_1$, $R_2$, $R_3$, and $R_4$, independently, are hydrogen or a $C_1$–$C_{10}$ alkyl group.

2. The compound of claim 1 wherein $R_1$, $R_2$, $R_3$, and $R_4$ each is hydrogen.

3. The compound of claim 1 wherein $R_1$, $R_2$, $R_3$, and $R_4$ each is a methyl group.

4. The compound of claim 1 wherein $R_1$, $R_2$, $R_3$, and $R_4$ each is an ethyl group.

5. The compound of claim 1 wherein $R_1$ and $R_2$ each is a methyl group, and $R_3$ and $R_4$ each is an ethyl group.

6. The compound (II) of claim 1 wherein $R_1$ and $R_2$ each is an ethyl group, and $R_3$ and $R_4$ each is a methyl group.

7. The compound of claim 1 wherein $R_1$, $R_2$, $R_3$, and $R_4$ each is an n-butyl group.